United States Patent
Lee et al.

(10) Patent No.: US 8,753,494 B2
(45) Date of Patent: Jun. 17, 2014

(54) GAS SENSOR AND PREPARING METHOD OF THE SAME

(75) Inventors: Youngmi Lee, Seoul (KR); Myung Hwa Kim, Uiwang-si (KR); Min-Cheol Oh, Busan (KR); Hyunkyung Do, Goyang-si (KR); Kyung Jang, Seoul (KR); Ji-Hyang Jang, Busan (KR)

(73) Assignee: Ewha University—Industry Collaboration Foundation, Seoul (KR)

( * ) Notice: Subject to any disclaimer, the term of this patent is extended or adjusted under 35 U.S.C. 154(b) by 54 days.

(21) Appl. No.: 13/587,090

(22) Filed: Aug. 16, 2012

(65) Prior Publication Data

US 2013/0043129 A1 Feb. 21, 2013

(30) Foreign Application Priority Data

Aug. 19, 2011 (KR) ........................ 10-2011-0082708

(51) Int. Cl.
*G01N 27/40* (2006.01)
*B82Y 40/00* (2011.01)
*B82Y 15/00* (2011.01)

(52) U.S. Cl.
USPC ......... 204/431; 977/840; 73/23.31; 73/23.32; 427/498; 427/512; 205/780.5; 205/782

(58) Field of Classification Search
USPC .................... 73/23.31, 23.32; 204/421–429; 977/840; 427/512
See application file for complete search history.

(56) References Cited

U.S. PATENT DOCUMENTS 6,280,878 B1 * 8/2001 Maruyama et al. ........... 429/233
2005/0126930 A1 * 6/2005 Prohaska et al. ........... 205/779.5

FOREIGN PATENT DOCUMENTS

KR 10-2009-0018787 2/2009

OTHER PUBLICATIONS

Shim et al. (Anal. Chem. 2009, 81, 8571-8576).*
Hyunkyung Do, "Development and Biological Applications of Nanopore Sensor of Electrochemical Current Measurement Type for Measuring Nitrogen Monoxide and Oxygen on Real Time Basis", Ehwa Womans University the Graduate School, Jan. 2011 (English abstract attached).
Confirmation of Thesis Service from Head Librarian of Central Library of EHWA Womans University, 2011.

* cited by examiner

*Primary Examiner* — Jennifer Dieterle
(74) *Attorney, Agent, or Firm* — Brundidge & Stanger, P.C.

(57) ABSTRACT

The present disclosure relates to a gas sensor including a nanopore electrode and a fluorine compound coated on the nanopore electrode, and also relates to a preparing method of the gas sensor.

9 Claims, 5 Drawing Sheets

FIG. 3 zpu
(perfluoroether diacrylate)

GAS SENSOR AND PREPARING METHOD OF THE SAME

CROSS-REFERENCE TO RELATED APPLICATION

This application claims the benefits of Korean Patent Application No. 10-2011-0082708 filed Aug. 19, 2011. The entire disclosure of the prior application is incorporated herein by reference in its entirety.

TECHNICAL FIELD

The present disclosure relates to a gas sensor including a nanopore electrode and a fluorine compound coated on the nanopore electrode, and also relates to a preparing method of the gas sensor.

BACKGROUND ART

Recently, there has been increased a demand for experiments of detecting oxygen ($O_2$) gas molecules and nitrogen monoxide (NO) gas molecules under biological conditions by using an electrochemical sensor. This is because oxygen gas molecules and nitrogen monoxide gas molecules act an important role as signaling molecules in vivo. Oxygen is essential to keep most living organisms alive, and nitrogen monoxide is important for biological and physiological processes such as vasodilatation and neurotransmission. The oxygen and the nitrogen monoxide closely interact with each other in vivo. By way of example, when temporary hypoxia occurs, the nitrogen monoxide acts as a signaling molecule for inducing vasodilatation, so that a sufficient amount of oxygen is supplied to solve the hypoxia.

Various methods have been used to effectively detect nitrogen monoxide and oxygen. However, particularly, a nitrogen monoxide gas has a short lifespan in a radical state and a very small amount of the nitrogen monoxide gas in a nanomolar concentration can be present in vivo, and, thus, the nitrogen monoxide gas is difficult to detect. Typically, a chemiluminescence method or electron paramagnetic resonance spectroscopy has been used as a method for detecting nitrogen monoxide. These methods are used to analyze a material produced as a result of a reaction between nitrogen monoxide and other materials. However, these methods require relatively complicated analysis and high cost, and, thus, it is difficult to apply these methods to real-time analysis in a biological system. Meanwhile, an electrochemical sensor immediately responds to a gas, and, thus, it can detect a gas before the gas disperses and disappears, and it is suitable for real-time analysis. However, there are many kinds of electrochemical sensors and capacity of a sensor is affected by a kind of a compound contained in an electrode of the sensor. Therefore, a study for developing a high-capacity electrochemical sensor is still needed.

In a sensor including an ultra microelectrode having a diameter on a micrometer or nanometer scale, a voltage drop phenomenon and a double-layer charging effect can be reduced and a material can be delivered to a surface of the electrode at high speed. Therefore, there have been many attempts to install an ultra microelectrode in a sensor to detect, in real-time, a concentration of a gas at each local position in the vicinity of a gas generation source.

By way of example, Korean Patent Application No. 10-2008-7027651 entitled "Nanopore particle analyzer, method of preparation and use thereof" describes a nanopore electrode as one of ultra microelectrodes. However, there is lack of research for maximizing an ability of a sensor for selectively sensing a gas by simultaneously controlling a kind of a compound contained in an electrode of the sensor and morphology of the electrode.

DISCLOSURE OF THE INVENTION

Problems to be Solved by the Invention

The present inventors manufactured a gas sensor including a nanopore electrode and a fluorine compound coated on the nanopore electrode, and found that if the gas sensor is used for detecting a gas, it is possible to selectively detect a diatomic gas depending on polarity. The present disclosure has been completed based on such findings.

The present disclosure provides a gas sensor including a nanopore electrode and a fluorine compound coated on the nanopore electrode and also provides a preparing method of the gas sensor.

However, the problems sought to be solved by the present disclosure are not limited to the above description and other problems can be clearly understood by those skilled in the art from the following description.

Means for Solving the Problems

In accordance with a first aspect of the present disclosure, there is provided a gas sensor including a nanopore electrode and a fluorine compound coated on the nanopore electrode.

In accordance with a second aspect of the present disclosure, there is provided a method for preparing the gas sensor in accordance with the first aspect of the present disclosure. The method includes preparing a nanopore electrode and coating a fluorine compound on the nanopore electrode.

Effect of the Invention

A gas sensor including a nanopore electrode and a fluorine compound coated on the nanopore electrode as prepared in accordance with the present disclosure can be used for measuring an electrochemical oxidation-reduction reaction of a diatomic gas such as oxygen and nitrogen monoxide. Detecting the diatomic gas such as oxygen and nitrogen monoxide is required in various fields from a biological system to development of a fuel cell electrode.

Particularly, the gas sensor in accordance with the present disclosure includes the fluorine compound, and, thus, if the gas sensor selectively detects oxygen mixed with a polar gas, sensitivity can be maximized. To be specific, if the gas sensor in accordance with the present disclosure is used, capacity for detecting oxygen is remarkably increased at an oxygen reduction potential (−0.6 V vs. Ag/AgCl) and nitrogen monoxide is not detected at a nitrogen monoxide oxidation potential. Accordingly, it is confirmed that the gas sensor in accordance with the present disclosure selectively responds to a gas depending on polarity. Further, since the fluorine compound is coated on a surface of a working electrode of the gas sensor, it is possible to increase sensitivity of the gas sensor and also possible to prevent the working electrode from being contaminated.

Furthermore, since the nanopore electrode having a diameter of about 800 nm to about 1.2 μm is provided in the gas sensor in accordance with the present disclosure, the gas sensor has high resolution and sensitivity can be increased due to an enlarged surface area. Moreover, since platinum is additionally coated on the working electrode, the surface area can be further increased and the sensitivity of the gas sensor can be maximized.

As for a conventional oxygen gas sensor, various ions are adsorbed onto a surface of platinum used as a working electrode of the sensor, resulting in reduction of a lifespan of the electrode. Therefore, an additional film coating is needed to prevent the electrode from ion absorption. Meanwhile, as for the gas sensor including the nanopore electrode coated with the fluorine compound in accordance with an illustrative embodiment, even if an additional film not coated, there is no problem of reduction of a lifespan of the electrode caused by ion absorption. Further, the gas sensor has high sensitivity by selectively responding to only a relatively nonpolar gas.

BRIEF DESCRIPTION OF THE DRAWINGS

Non-limiting and non-exhaustive embodiments will be described in conjunction with the accompanying drawings. Understanding that these drawings depict only several embodiments in accordance with the disclosure and are, therefore, not to be intended to limit its scope, the disclosure will be described with specificity and detail through use of the accompanying drawings, in which.

BEST MODE FOR CARRYING OUT THE INVENTION

Hereinafter, illustrative embodiments and examples will be described in detail so that inventive concept may be readily implemented by those skilled in the art.

However, it is to be noted that the present disclosure is not limited to the illustrative embodiments and examples but can be realized in various other ways. In drawings, parts irrelevant to the description are omitted for the simplicity of explanation, and like reference numerals denote like parts through the whole document.

Through the whole document, the term "comprises or includes" and/or "comprising or including" used in the document means that one or more other components, steps, operation and/or existence or addition of elements are not excluded in addition to the described components, steps, operation and/or elements unless context dictates otherwise.

Through the whole document, the term "on" that is used to designate a position of one element with respect to another element includes both a case that the one element is adjacent to the another element and a case that any other element exists between these two elements.

Through the whole document, the term "combination of" included in Markush type description means mixture or combination of one or more components, steps, operations and/or elements selected from the group consisting of components, steps, operation and/or elements described in Markush type and thereby means that the disclosure includes one or more components, steps, operations and/or elements selected from the Markush group.

The term "about or approximately" or "substantially" are intended to have meanings close to numerical values or ranges specified with an allowable error and intended to prevent accurate or absolute numerical values disclosed for understanding of the present disclosure from being illegally or unfairly used by any unconscionable third party. Through the whole document, the term "step of" does not mean "step for".

Through the whole document, the term "diatomic gas" or "diatomic molecular gas" used in the document means a gas molecule containing two atoms and may include a gas molecule containing two same atoms, for example, but not limited to, an oxygen gas, or a gas molecule containing two different atoms, for example, but not limited to, a nitrogen monoxide gas.

Hereinafter, illustrative embodiments and examples will be explained in detail with reference to the accompanying drawings.

In accordance with a first aspect of the present disclosure, there is provided gas sensor including a nanopore electrode and a fluorine compound coated on the nanopore electrode.

In accordance with the illustrative embodiment, the nanopore electrode may include, but is not limited to, platinum. In order to increase sensitivity of a sensor, a surface area of a working electrode needs to be increased. Thus, the electrode of the sensor may be platinized by an electrochemical deposition method using a platinum precursor-containing solution, but it is not limited thereto. Further, the nanopore electrode which is not yet platinized may be made of platinum wire and may contain platinum therein, but it is not limited thereto.

By way of example, a pore of the nanopore electrode may have a diameter of, but not limited to, about 800 nm to about 1.2 μm. By way of example, the pore of the nanopore electrode may have a diameter of, but not limited to, about 800 nm to about 900 nm, about 800 nm to about 1 μm, about 800 nm to about 1.1 μm, about 800 nm to about 1.2 μm, about 900 nm to about 1 μm, about 900 nm to about 1.1 μm, about 900 nm to about 1.2 μm, about 1 μm to about 1.1 μm, about 1 μm to about 1.2 μm, or about 1.1 μm to about 1.2 μm. Since the prepared nanopore electrode is used in the gas sensor, the sensor may have, but is not limited to, high resolution and high sensitivity due to an enlarged surface area of the electrode.

In accordance with the illustrative embodiment, the fluorine compound may be coated on the nanopore electrode by, but not limited to, polymerization of a fluorinated photocurable monomer with photocuring. A light source for the photocuring is not limited to a specific light source. By way of example, a light source for the photocuring may include, but is not limited to, a medium pressure mercury lamp, a high pressure mercury lamp, a $N_2$ laser, or an $Ar^+$ laser. Further, by way of example, photocuring polymerization using an UV curing device may be performed, but the present disclosure is not limited thereto.

Figure 4:
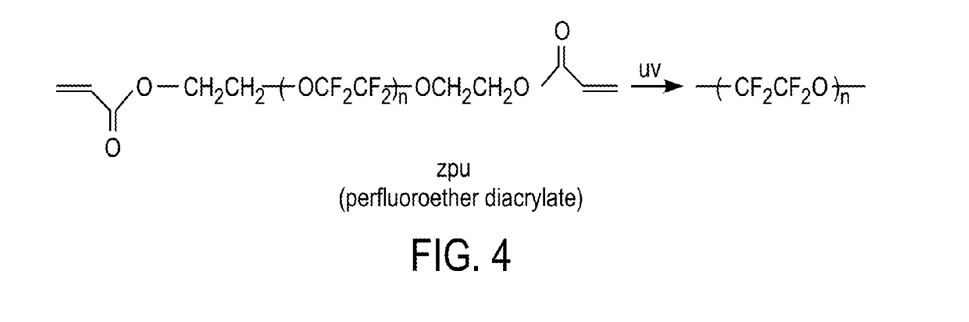
FIG. 4 is a mechanism in which ZPU (perfluoroether diacrylate) as one of fluorinated photocurable monomers is polymerized by UV curing during a fluorination process onto a nanopore electrode in accordance with an example.

In this regard, FIG. 4 is a mechanism in which ZPU (perfluoroether diacrylate) as one of fluorinated photocurable monomers is polymerized by UV curing during a fluorination process onto a nanopore electrode when a gas sensor is manufactured in accordance with an example. Perfluoroether group contained in the ZPU has a structure similar to a structure of Teflon [(CF$_2$CF$_2$)$_n$], but its structure is more efficient in penetration of an oxygen gas than the structure of Teflon. By way of example, in accordance with an example, when a double bond of an acrylic group contained in the ZPU is broken by UV irradiation of about 365 nm emitted from a medium pressure mercury lamp, consecutive polymerization is induced and a three-dimensional transparent and thin film may be formed, but the present disclosure is not limited thereto.

In accordance with the illustrative embodiment, the fluorinated photocurable monomer may include, but is not limited to, at least one acrylate group as a fluorinated photocurable functional group.

In accordance with the illustrative embodiment, the fluorinated photocurable monomer may include a monomer selected from the group consisting of, but not limited to, perfluoro-1,6-hexanediol diacrylate, perfluoro tetraethylene glycol diacrylate, octafluorobiphenyl diacrylate, tetrafluorophenyl monoacrylate, perfluoro triethylene glycol diacrylate, perfluoro-1,8-octanediol diacrylate, perfluoro-1,10-decanediol diacrylate, and combinations thereof. By way of example, when a fluorine compound is coated on the nanopore electrode by polymerization of a fluorinated photocurable monomer with photocuring, a mixture containing, but not limited to, perfluoro-1,6-hexanediol diacrylate, perfluoro tetraethylene glycol diacrylate, octafluorobiphenyl diacrylate, tetrafluorophenyl monoacrylate, and a photoinitiator at a ratio of about 50:30:10:5:5 may be used.

By way of example, the fluorinated photocurable monomer includes at least one acrylate group as a fluorinated photocurable functional group and may include, but is not limited to, one or more compounds expressed in the following Formulas 1 to 4.

[Formula 1]

[Formula 2]

[Formula 3]

[Formula 4]

Formula 1 represents perfluoro-1,6-hexanediol diacrylate; Formula 2 represents perfluoro tetraethylene glycol diacrylate; Formula 3 represents octafluorobiphenyl diacrylate; and Formula 4 represents tetrafluorophenyl monoacrylate.

In accordance with the illustrative embodiment, the fluorine compound may be coated on the nanopore electrode as a thin film having a thickness of, but not limited to, from about 100 nm to about 1 μm. By way of example, the fluorine compound may be coated on the nanopore electrode as a thin film having a thickness of, but not limited to, from about 100 nm to about 300 nm, about 100 nm to about 500 nm, about 100 nm to about 800 nm, about 100 nm to about 1 μm, about 300 nm to about 500 nm, about 300 nm to about 800 nm, about 300 nm to about 1 μm, about 500 nm to about 800 nm, about 500 nm to about 1 μm, or about 800 nm to about 1 μm. The nanopore electrode of the gas sensor may contain the fluorine compound as a thin film having a thickness of about 1 μm or less, so that it is possible to selectively allow penetration of diatomic gases depending on polarity. Further, since the fluorine compound is coated on the nanopore electrode of the gas sensor, it is possible to increase sensitivity of the gas sensor and also possible to prevent the working electrode from being contaminated. By way of example, a sensor including the nanopore electrode coated with the fluorine compound in accordance with the illustrative embodiment does not have a problem of, but not limited to, reduction of a lifespan of the electrode caused by unnecessary ion adsorption, even if there is no additional film.

In accordance with the illustrative embodiment, the gas sensor may further include, but is not limited to, platinum coated on the fluorine compound. If platinization is further performed on the fluorine compound coated on the nanopore electrode, it is possible to further increase the surface area of the electrode and also possible to maximize the sensitivity of the sensor, but the present disclosure is not limited thereto.

In accordance with the illustrative embodiment, the gas sensor may include, but is not limited to, a sensor having polarity dependent-sensing ability which can be used to selectively sense a gas containing two atoms. The term "gas containing two atoms" means the term "diatomic gas" defined above. By way of example, if a nitrogen monoxide gas as a diatomic gas and an oxygen gas as another diatomic gas are mixed, the gas sensor has higher sensitivity to the oxygen gas as a relatively nonpolar gas due to a fluorine compound layer, and, thus, the gas sensor can distinguish and sense gases based on a difference in sensitivity depending on polarity. Generally, polarity of a material is a relative concept. By way of example, in a comparison between the nitrogen monoxide gas and the oxygen gas, the oxygen gas is much more nonpolar. Since the nitrogen monoxide gas is formed of a nitrogen atom having an electronegativity of about 3.0 and an oxygen atom having an electronegativity of about 3.5, it has a little polarity. Meanwhile, since the oxygen gas is formed of two same atoms, a polarizing phenomenon does not occur in a molecule of the oxygen gas. The gas sensor in accordance with the present disclosure distinguishes and senses gases by using a difference in relative polarity between diatomic gas molecules. By way of example, if the gas sensor in accordance with the present disclosure is used, capacity for detecting oxygen is remarkably increased at an oxygen reduction potential (−0.6 V vs. Ag/AgCl) and nitrogen monoxide is not detected at a nitrogen monoxide oxidation potential. Accordingly, it is confirmed that the gas sensor in accordance with the present disclosure selectively responds to a gas depending on polarity.

In accordance with the illustrative embodiment, the gas sensor may include, but is not limited to, a sensor which can be used to selectively sense an oxygen gas.

In accordance with a second aspect of the present disclosure, there is provided a method for preparing the gas sensor of the first aspect. The method includes preparing a nanopore electrode and coating a fluorine compound on the nanopore electrode.

The method of the second aspect is provided for preparing the gas sensor of the first aspect. Therefore, all the illustrative embodiments and examples as they are can be applied to the second aspect, but the present disclosure is not limited thereto.

Figure 1:
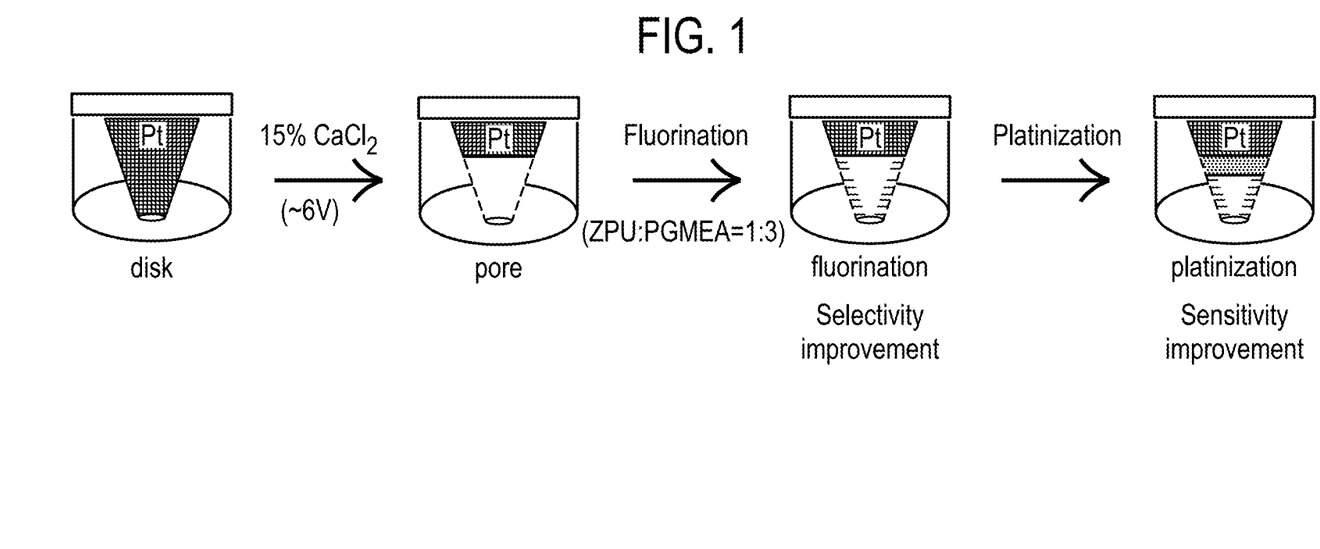
FIG. 1 is a flow chart showing a process of preparing a gas sensor in accordance with an example.

Regarding the second aspect of the present disclosure, FIG. 1 is a flow chart showing a process of preparing a gas sensor in accordance with an example. To be specific, in FIG. 1, the process of preparing the gas sensor includes four steps: a step of forming a disk electrode; a step of forming a nanopore electrode by additionally etching the disk electrode; a step of controlling gas sensitivity depending on polarity by coating a fluorine compound on the nanopore electrode; and a step of increasing a surface area and sensitivity of the gas sensor by additionally depositing porous platinum on the fluorine compound layer.

In accordance with the illustrative embodiment, the fluorine compound may be coated on the nanopore electrode by, but not limited to, dipping the nanopore electrode to a solution containing a fluorinated photocurable monomer, and polymerizing the fluorinated photocurable monomer with photocuring. A light source for the photocuring is not limited to a specific light source. By way of example, a light source for the photocuring may include, but is not limited to, a medium pressure mercury lamp, a high pressure mercury lamp, a $N_2$ laser, or an $Ar^+$ laser. Further, by way of example, photocuring polymerization using an UV curing device may be performed, but the present disclosure is not limited thereto.

In this regard, FIG. 4 is a mechanism in which ZPU (perfluoroether diacrylate) as one of fluorinated photocurable monomers is polymerized by UV curing with UV rays during a fluorination process onto a nanopore electrode when a gas sensor is manufactured in accordance with an example. Perfluoroether contained in the ZPU has a structure similar to a structure of Teflon [$(CF_2CF_2)_n$], but its structure is more efficient in penetration of an oxygen gas than the structure of Teflon. By way of example, in accordance with an example, when a double bond of an acrylic group contained in the ZPU is broken by UV rays of about 365 nm emitted from a medium pressure mercury lamp, consecutive polymerization is induced and a three-dimensional transparent and thin film may be formed, but the present disclosure is not limited thereto.

In accordance with the illustrative embodiment, the fluorinated photocurable monomer may include, but is not limited to, at least one acrylate group as a fluorinated photocurable functional group.

In accordance with the illustrative embodiment, the fluorinated photocurable monomer may include a monomer selected from the group consisting of, but not limited to, perfluoro-1,6-hexanediol diacrylate, perfluoro tetraethylene glycol diacrylate, octafluorobiphenyl diacrylate, tetrafluorophenyl monoacrylate, perfluoro triethylene glycol diacrylate, perfluoro-1,8-octanediol diacrylate, perfluoro-1,10-decanediol diacrylate, and combinations thereof. By way of example, when a fluorine compound is coated on the nanopore electrode by polymerization of a fluorinated photocurable monomer with photocuring, a mixture containing, but not limited to, perfluoro-1,6-hexanediol diacrylate, perfluoro tetraethylene glycol diacrylate, octafluorobiphenyl diacrylate, tetrafluorophenyl monoacrylate, and a photoinitiator at a ratio of about 50:30:10:5:5 may be used.

By way of example, the fluorinated photocurable monomer includes at least one acrylate group as a fluorinated photocurable functional group and may include, but is not limited to, one or more compounds expressed in the following Formulas 1 to 4.

Formula 1 represents perfluoro-1,6-hexanediol diacrylate; Formula 2 represents perfluoro tetraethylene glycol diacrylate; Formula 3 represents octafluorobiphenyl diacrylate; and Formula 4 represents tetrafluorophenyl monoacrylate.

In accordance with the illustrative embodiment, the solution containing the fluorinated photocurable monomer may further include, but is not limited to, a photoinitiator. By using the photoinitiator, polymerization of the fluorinated photocurable monomer by photocuring may be accelerated, but the present disclosure is not limited thereto. By way of example, the photoinitiator may include a photoinitiator selected from the group consisting of, but not limited to, 1-hydroxy cyclohexylphenylketone, α,α-dimethyl-α-hydroxy acetophenone, 1-[4-(2-hydroxyethoxy)phenyl]-2-hydroxy-2-methyl-propane-1-one, α,α-dethoxyacetophenone (DEAP), benzildimethyl ketal (BDK), benzophenone, and combinations thereof.

In accordance with the illustrative embodiment, the method of preparing the gas sensor further includes, but is not limited to, depositing porous platinum on the fluorine compound after coating the fluorine compound on the nanopore electrode. If platinum is additionally deposited, it is possible to further increase the surface area of the electrode and also possible to maximize the sensitivity of the sensor, but the present disclosure is not limited thereto.

The gas sensor prepared in accordance with the present disclosure selectively distinguishes and senses a relatively nonpolar gas based on a difference in polarity between diatomic gases such as a nitrogen monoxide gas and an oxygen gas. The gas sensor is useful for in-vivo and in-vitro experiments for analyzing biological samples and also useful for rapidly measuring a local concentration of a gas. A typical oxygen gas sensor has a problem of reduction of a lifespan of an electrode caused by absorption of various ions, which includes ions reduced at an oxygen reduction potential simultaneously, on a surface of the electrode. Therefore, forming an additional film is needed to prevent the electrode from ion absorption. Meanwhile, the sensor including the nanopore electrode coated with the fluorine compound in accordance with the illustrative embodiment, selectively responds to only nonpolar gases such as an oxygen gas even if there is no additional film, and has high sensitivity.

Hereinafter, examples will be explained in detail, but the illustrative embodiments are not limited thereto.

EXAMPLES

In the present example, a gas sensor was prepared in accordance with a process shown in FIG. 1 and sensitivity of the gas sensor was electrochemically analyzed. Hereinafter, a process for preparing the gas sensor and a process for analyzing sensitivity of the gas sensor will be explained in detail.

1. Reagent Used for Experiment

In order to increase sensitivity of a sensor, a surface area of a working electrode needed to be increased. In order to do so, the electrode of the sensor was platinized by an electrochemical deposition method in the present example. A platinum precursor-containing solution (platinizing solution) used to platinize the electrode was a product of YSI Incorporated (Yellow springs, Ohio 45387 USA).

Further, in order to prepare Ag/AgCl as a reference electrode of the sensor, Ag wire was immersed and oxidized in an appropriate solution to prepare AgCl. Herein, iron(III) chloride hexahydrate used to prepare the solution was a product of Samchun Chemicals.

Further, sulfuric acid used to prepare a 0.1 M sulfuric acid solution used as a standard solution for acquiring a dynamic response curve of a sensor including a nanopore electrode coated with a fluorine compound was a product of Sigma-Aldrich (St. Louis, Mo.).

Furthermore, as represented in FIG. 1, a conical sharp-pointed nanopore electrode was formed by etching a disk electrode in an etching solution. The etching solution was prepared with $CaCl_2$ and acetone, and both of them were products of Sigma-Aldrich.

Moreover, ferrocenemethanol (Fc), tetrabutylammonium tetrafluoroborate ($TBABF_4$), and acetonitrile ($CH_3CN$) used to prepare a solution required for measuring a current-voltage (CV) of the prepared sensor were products of Sigma-Aldrich.

In addition, propylene glycol monomethyl ether acetate (PGMEA) used to prepare a solution containing ZPU 13-455 and PGMEA at a ratio of about 1:5 for coating a fluorine compound during the process for preparing the sensor was a product of Sigma-Aldrich.

2. Preparation of Nanopore Electrode

In the gas sensor of the present example, a Pt working electrode (WE) coated with platinum and a reference electrode/counter electrode (RE/CE) prepared by using the coil-shaped Ag/AgCl wire was used as electrodes.

The working electrode (WE) was prepared as follows. By using an Ag epoxy (Alfa-Aesar), platinum wire (Goodfellow, 99.99%) having a length of about 1 cm and a diameter of about 25 μm was connected to copper wire (Alpha) having a length of about 5 cm to form platinum/copper wire. The platinum/copper wire was heated in an oven at about 80° C. for about 15 minutes to harden the Ag epoxy. The thus-prepared platinum/copper wire was inserted into a soda lime glass capillary (Dagan Corporation, LB16 OD=1.65 mm, ID=1.10 mm soften at 700° C.) having an appropriate length, such that an end of the platinum wire was exposed by about 5 mm. By using a micromanipulator, about 30 μm of the exposed end of the platinum wire out of the soda lime glass capillary was immersed in a $CaCl_2$ solution (acetone:water=1:2 used as a solvent, concentration of about 1.2 M). Then, by using a variable voltmeter, AC voltage of about 5 V was applied between the platinum/copper wire and a platinum counter electrode having a large area to perform an electrochemical etching process thereto. As a result, a conical sharp Pt tip was prepared, and it was observed with an optical microscope as shown in a photo entitled "etched Pt tip" in FIG. 2.

Thereafter, the platinum/copper wire was completely pushed into the soda lime glass capillary and a distance from a pore of the capillary to the end of the platinum wire was controlled to be a diameter of a nanopore to be formed in the electrode. The capillary was fused by a torch to seal the pore and the sharp end of the platinum wire. At that time, the pore and the sharp end of the platinum wire were sealed so as not to form air bubbles around the sealed metal with care. The opposite inlet side of the soda lime glass capillary, where a sheath of the copper wire was exposed, was processed with epoxy (Permatex) for about 5 minutes so as to be connected to the sheath of the copper wire and dried for about 10 minutes. Meanwhile, a thickness glass part of the soda lime glass capillary, where the platinum wire was sealed, was trimmed by using a finer grit sandpaper to prepare a nanoscale disk electrode in which the end of the platinum wire was exposed. Herein, desirably, a diameter of the disk electrode was about 500±100 nm. The disk electrode was observed with an optical microscope as shown in a photo entitled "disk" in FIG. 2.

In order to prepare the Ag/AgCl reference electrode (RE), a sheath of silver wire (AM systems) having a diameter of about 125 μm and a length of about 10 cm was peeled off. The silver wire of about 6 cm was coiled in a coil shape around a glass electrode and then separated from the electrode, and only a coil-shaped part was immersed in a 0.1 M $FeCl_3$ solution. After about one minute, the silver wire was observed to be oxidized and turned into black. Then, the silver wire was washed with distilled water. The thus-prepared Ag/AgCl reference electrode in a coil shape served as a reference electrode and a counter electrode simultaneously due to the nature of an ultra micro-structural sensor.

After the Ag/AgCl electrode was prepared, the Ag/AgCl electrode was coiled again in a coil shape around the prepared platinum working electrode to form a nanoscale disk electrode. The radius (r) of the nanoscale disk electrode was calculated by substituting a limiting current of the cyclic voltammetry (CV) curve obtained in 5 mM ferrocene ($CH_3CN$ containing ferrocenemethanol and 0.1 M $TBABF_4$) to the following equation (1). A voltage of the CV was in a range of from about −0.3 V to about 0.7 V:

$$i_{ss} = 4nFD_oC_or \quad [1]$$

In the equation (1), $i_{ss}$ represented a mass-transport limiting current (A) of the CV; n represented the number of electrons at an oxidation-reduction reaction of ferrocene as 1; F represented a Faraday constant as 96485.34 C/mol; $D_o$ represented a diffusion coefficient of ferrocene as $2.4 \times 10^{-5}$ cm$^2$/s; $C_o$ represented a concentration of ferrocene as 5 mM; and r represented the radius of the nanoscale disk electrode to be calculated.

In order to prepare the nanopore electrode, the nanoscale disk electrode prepared as described above was additionally etched in the CaCl$_2$ solution (acetone:water=1:2 used as a solvent, concentration of about 1.2 M). A height of the CaCl$_2$ solution in an experimental cell was adjusted to be equal to a height of distilled water in an ultrasonic bath (Saehan cleaner), and a sonicator was turned on. Then, an end of the platinum disk electrode was positioned to be slightly higher than the platinum counter electrode. While heights thereof were adjusted, the platinum counter electrode and the platinum disk working electrode in sequence were slightly immersed in the vibrating CaCl$_2$ solution. Thereafter, a voltage of about 5 V was applied between the counter electrode and the working electrode to perform an etching process for about 2 seconds. While the sonicator was turned on, the both electrodes were taken out of the CaCl$_2$ solution, and then the sonicator and the variable voltmeter were turned off. The both electrodes taken out of the CaCl$_2$ solution were washed with first distilled water, and immersed in third distilled water to perform ultrasonication for about 10 seconds. As a result, a neatly etched surface of the platinum electrode was obtained.

Figure 2:
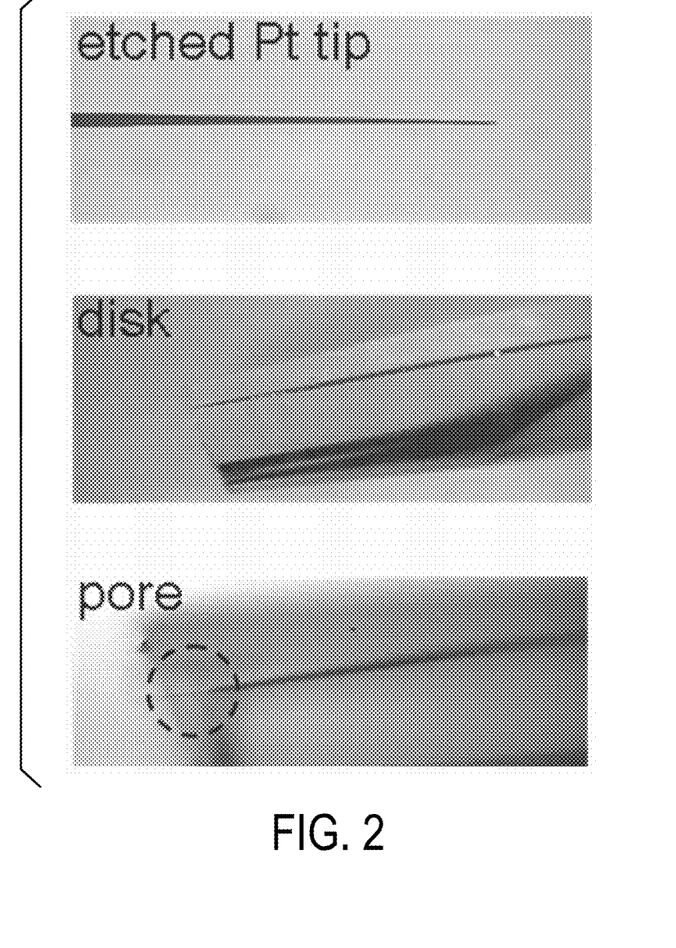
FIG. 2 is photo images taken during a process of preparing a nanopore electrode containing platinum in accordance with an example.
Figure 3:
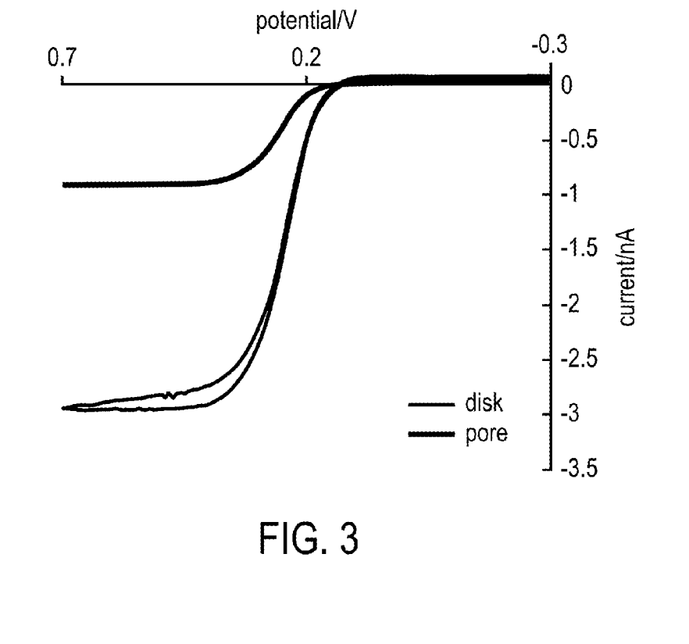
FIG. 3 is a cyclic voltammetry curve for confirming that pores are formed in a nanopore electrode prepared in accordance with an example.

Formation of a nanopore in the sensor electrode prepared in accordance with the present example was checked with the optical microscope as shown in a photo entitled "pore" in FIG. 2. Further, as shown in FIG. 3, a decrease in a limiting current of the CV curve in the ferrocene solution confirmed that a nanopore was formed in the sensor electrode.

3. Fluorine Compound Coating on Nanopore Electrode

The nanopore electrode prepared in accordance with the present example was dipped in the solution (ZPU 13-455: PGMEA=1:5) to be sonicated for about 10 seconds, and the nanopore electrode was maintained for about 30 minutes such that the solution containing fluorinated photocurable monomers could be absorbed into the nanopore and onto a glass surface. Then, the nanopore electrode was taken out of the solution and a nitrogen gas was introduced into the nanopore for about 30 seconds so as to prevent the nanopore from being clogged. Thereafter, the nanopore electrode was put into a UV curing device including a medium pressure mercury lamp and hardened in a nitrogen atmosphere for about 20 minutes. As a result, the fluorine compound was coated on the nanopore electrode.

In this regard, FIG. 4 shows a mechanism in which ZPU (perfluoroether diacrylate) as one of fluorinated photocurable monomers is polymerized by UV curing during a fluorination process onto a nanopore electrode in accordance with the present example.

4. Electrochemical Analysis on Sensing Ability of Sensor

The nanopore sensor prepared in accordance with the present example was calibrated by using an electrochemical analyzer (CHI 1000A, CHI Instruments) to analyze sensitivity of the gas sensor in accordance with the present example to an oxygen gas and a nitrogen monoxide gas.

To be specific, the gas sensor was calibrated with respect to the oxygen gas and the nitrogen monoxide gas as follows. A 0.1 M H$_2$SO$_4$ solution of about 2.5 mL was put in a mL 3-neck vial, and the electrode of the gas sensor prepared in accordance with the present example was put into the vial through one of the three necks to be immersed in the H$_2$SO$_4$ solution. Then, the other two necks were sealed with rubber stoppers. The electrochemical analyzer was connected to the electrode and a potential of about −0.6 V (vs. Ag/AgCl) was applied thereto, and an i-t curve was recorded. To be specific, for calibration with respect to the oxygen (O$_2$) gas, an oxygen stock solution (1.3 mM, 0.1 M H$_2$SO$_4$) was introduced in the amount of about 5 μL four times and 10 μL four times in sequence and an i-t curve was recorded. Meanwhile, for calibration with respect to the nitrogen monoxide (NO) gas, a nitrogen monoxide stock solution (1.91 mM, 0.1 M H$_2$SO$_4$) was introduced in the amount of about 1.25 μL three times and 2.5 μL three times in sequence and an i-t curve was recorded. The i-t curves were used to obtain a calibration curve (x-axis=O$_2$ or NO concentration/μM, y-axis=current/nA).

The oxygen stock solution used in the present example was prepared by putting the 0.1 M H$_2$SO$_4$ solution of about 5 mL into a 10 mL vial, sealing the vial with a rubber stopper, and purging oxygen for about 20 minutes. Meanwhile, the nitrogen monoxide stock solution used in the present example was prepared by putting the 0.1 M H$_2$SO$_4$ solution of about 5 mL into a 10 mL vial, sealing the vial with a rubber stopper, purging argon for about 30 minutes to remove all gases, and additionally purging nitrogen monoxide for about 20 minutes.

5. Electrochemical Analysis on Sensitivity of Sensor

The "electrochemical analysis on sensing ability of sensor" described above in paragraph No. 4 was applied to the gas sensor prepared in accordance with the present example, and a dynamic response curve and a corresponding calibration curve were obtained with respect to each of the oxygen gas and the nitrogen monoxide gas. The "gas sensor prepared in accordance with the present example" included four kinds of sensors which were prepared as gas sensors in accordance with the respective steps of FIG. 1. That is, an electrochemical analysis was carried out to each of a sensor including a disk electrode ("disk" of FIG. 1, hereinafter referred to as "disk"), a sensor including a nanopore electrode prepared by additionally etching the disk electrode ("pore" of FIG. 1, hereinafter referred to as "pore"), a sensor including the nanopore electrode coated with a fluorine compound ("fluorination" of FIG. 1, hereinafter referred to as "F"), and a sensor including the fluorine compound-coated electrode additionally coated platinum ("platinization" of FIG. 1, hereinafter referred to as "Pt").

Figure 5:
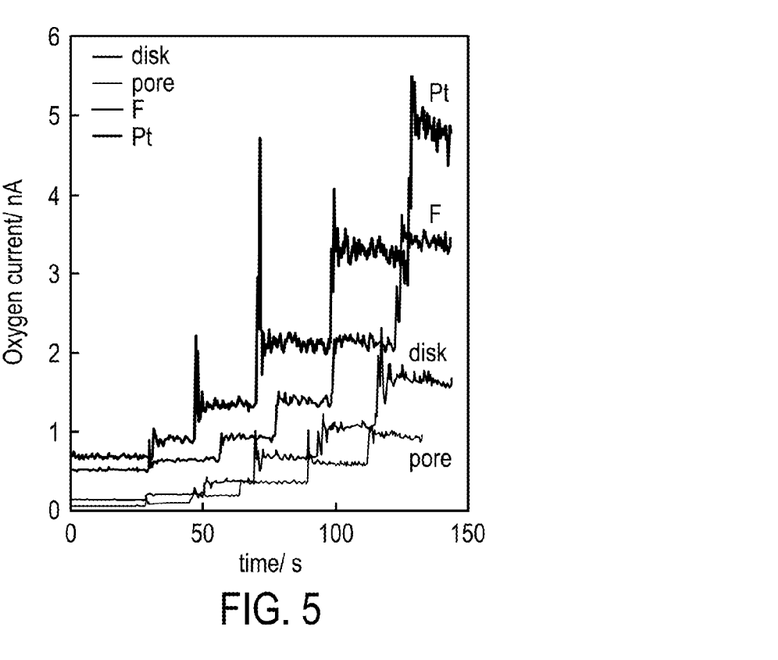
FIG. 5 is a dynamic current response curve showing sensitivity of a gas sensor prepared in accordance with an example to an oxygen gas.
Figure 6:
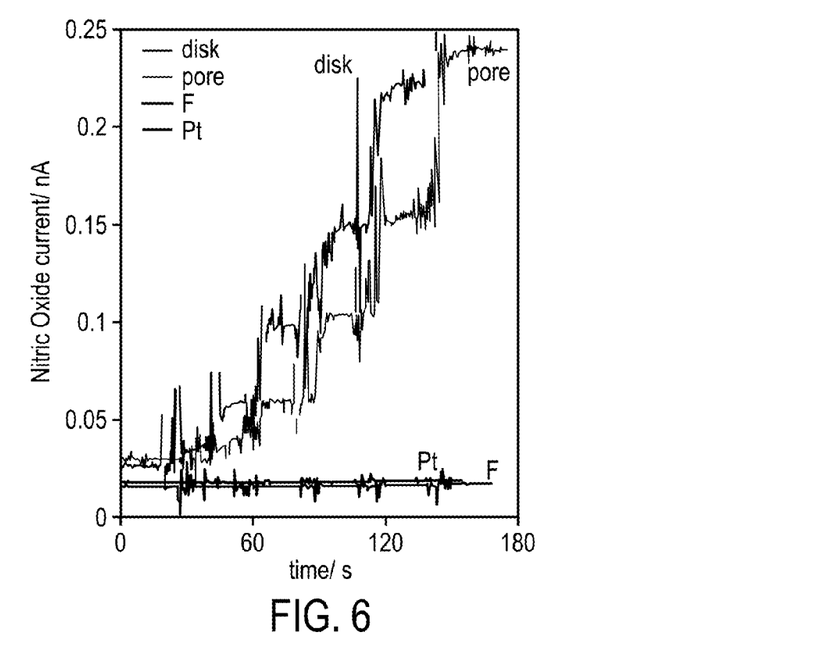
FIG. 6 is a dynamic current response curve showing sensitivity of a gas sensor prepared in accordance with an example to a nitrogen monoxide gas.
Figure 7:
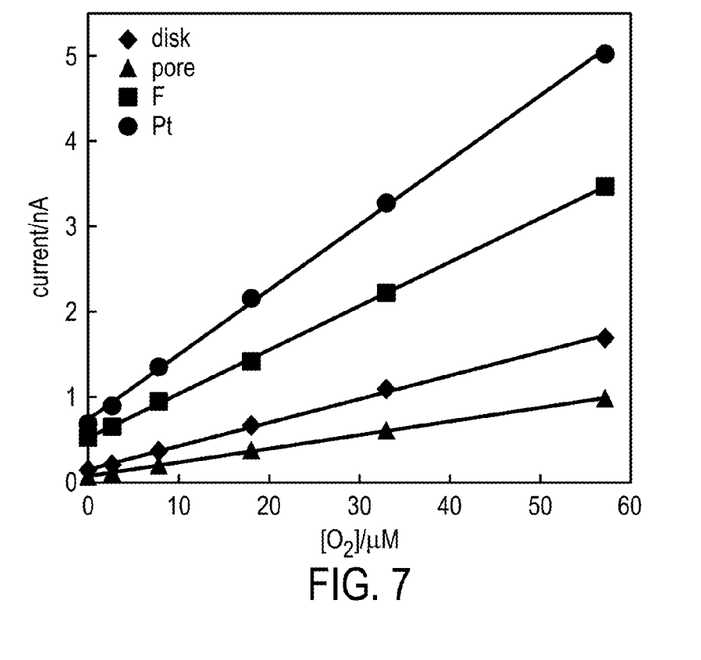
FIG. 7 is a corresponding calibration curve to FIG. 5 showing sensitivity of a gas sensor prepared in accordance with an example to an oxygen gas.
Figure 8:
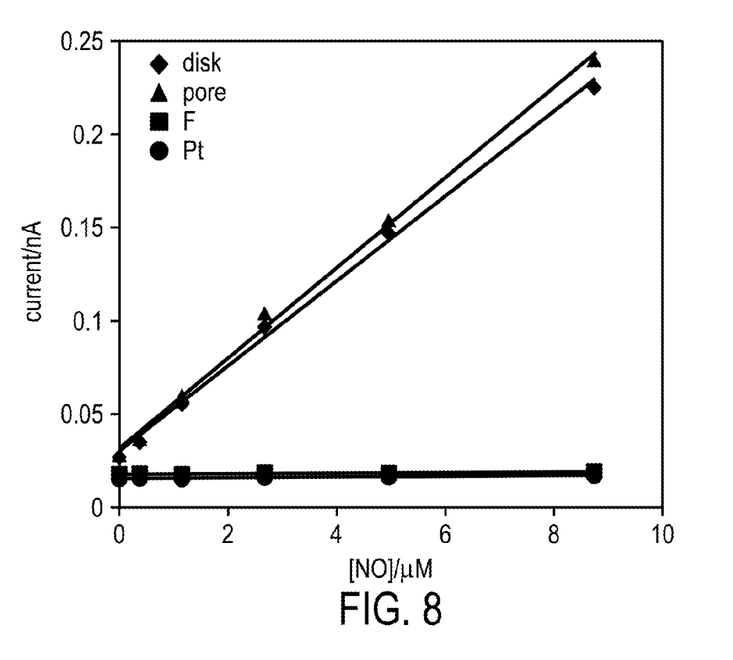
FIG. 8 is a corresponding calibration curve to FIG. 6 showing sensitivity of a gas sensor prepared in accordance with an example to a nitrogen monoxide gas.

FIGS. 5 to 8 show results of the electrochemical analysis on sensitivity of the respective four sensors. In this regard, FIG. 5 is a dynamic response curve showing sensitivity of a gas sensor in accordance with the present example to an oxygen gas. FIG. 6 is a dynamic response curve showing sensitivity of a gas sensor in accordance with the present example to a nitrogen monoxide gas. FIG. 7 is a corresponding calibration curve to FIG. 5 showing sensitivity of a gas sensor in accordance with the present example to an oxygen gas. FIG. 8 is a corresponding calibration curve to FIG. 6 showing sensitivity of a gas sensor in accordance with the present example to a nitrogen monoxide gas.

In all of the four sensors, a dynamic response curve was proportional to a concentration of a gas-saturated solution (0.1 M H$_2$SO$_4$), and a corresponding calibration curve had a correlation coefficient of about 0.998 or more.

Referring to FIGS. 5 to 8, sensitivity of the gas sensors to a gas was most affected by whether the fluorine compound was coated or not. The sensitivity to the oxygen gas of the two sensors (F and Pt), each of which included the electrode coated with the fluorine compound, was three times or more higher than that of the other two sensors (disk and pore). To be specific, the sensitivity was increased from about 15.9 pA/μM to about 51.3 pA/μM. However, the sensitivity to the nitrogen monoxide gas of the two sensors (F and Pt), each of which included the electrode coated with the fluorine compound, was sharply lower than that of the other two sensors (disk and pore). To be specific, the sensitivity was decreased from about 24.2 pA/μM to about 0.13 pA/μM.

From the above-described experimental results, it can be seen that if a gas sensor including a nanopore electrode coated with a fluorine compound is used to sense an oxygen gas, sensitivity to the oxygen gas is expected to be increased. Further, by using a sensitivity value (A/M) checked from a dynamic response curve before the gas sensor including a nanopore electrode coated with a fluorine compound is used, a concentration of the oxygen gas contained in an unknown sample can be calculated.

The above description of the present disclosure is provided for the purpose of illustration, and it would be understood by those skilled in the art that various changes and modifications may be made without changing technical conception and essential features of the present disclosure. Thus, it is clear that the above-described embodiments are illustrative in all aspects and do not limit the present disclosure. For example, each component described to be of a single type can be implemented in a distributed manner. Likewise, components described to be distributed can be implemented in a combined manner.

The scope of the present disclosure is defined by the following claims rather than by the detailed description of the embodiment. It shall be understood that all modifications and embodiments conceived from the meaning and scope of the claims and their equivalents are included in the scope of the present disclosure.

What is claimed is:

1. A gas sensor, comprising:
   a nanopore electrode; and
   a fluorine compound coated on the nanopore electrode,
   wherein the fluorine compound is coated on the nanopore electrode by polymerization of a fluorinated photocurable monomer with photocuring, and
   wherein the fluorinated photocurable monomer includes a monomer selected from the group consisting of perfluoro-1,6-hexanediol diacrylate, perfluoro tetraethylene glycol diacrylate, octafluorobiphenyl diacrylate, tetrafluorophenyl monoacrylate, perfluoro triethylene glycol diacrylate, perfluoro-1,8-octanediol diacrylate, perfluoro-1,10-decanediol diacrylate, and combinations thereof.

2. The gas sensor of claim 1, wherein the nanopore electrode includes platinum.

3. The gas sensor of claim 1, wherein the fluorine compound is coated on the nanopore electrode as a thin film having a thickness of from about 100 nm to about 1 μm.

4. The gas sensor of claim 1, wherein the gas sensor further includes platinum coated on the fluorine compound.

5. The gas sensor of claim 1, wherein the gas sensor includes a sensor having polarity dependent-sensing ability which can be used to selectively sense a gas containing two atoms.

6. The gas sensor of claim 1, wherein the gas sensor includes a sensor which can be used to selectively sense an oxygen gas.

7. A method for preparing the gas sensor of claim 1, the method comprising:
   preparing a nanopore electrode; and
   coating a fluorine compound on the nanopore electrode,
   wherein the fluorine compound is coated on the nanopore electrode by dipping the nanopore electrode to a solution containing a fluorinated photocurable monomer, and polymerizing the fluorinated photocurable monomer with photocuring, and
   wherein the fluorinated photocurable monomer includes a monomer selected from the grout consisting of perfluoro-1,6-hexanediol diacrylate, perfluoro tetraethylene glycol diacrylate, octafluorobiphenyl diacrylate, tetrafluorophenyl monoacrylate, perfluoro triethylene glycol diacrylate perfluoro-1,8-octanediol diacrylate, perfluoro-1,10-decanediol diacrylate, and combinations thereof.

8. The method of claim 7,
   wherein the solution containing the fluorinated photocurable monomer further includes a photoinitiator.

9. The method of claim 7, further comprising:
   coating platinum on the fluorine compound after coating the fluorine compound on the nanopore electrode.

\* \* \* \* \*